(12) United States Patent
Dakin et al.

(10) Patent No.: US 8,211,163 B2
(45) Date of Patent: Jul. 3, 2012

(54) HYBRID SYMMETRICAL STENT DESIGNS

(75) Inventors: Greg Dakin, Minneapolis, MN (US); Brian Tischler, New Brighton, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 820 days.

(21) Appl. No.: 11/768,310

(22) Filed: Jun. 26, 2007

(65) Prior Publication Data

US 2008/0065194 A1 Mar. 13, 2008

Related U.S. Application Data

(60) Provisional application No. 60/844,307, filed on Sep. 13, 2006.

(51) Int. Cl.
*A61F 2/06* (2006.01)

(52) U.S. Cl. .................................. 623/1.15; 623/1.1

(58) Field of Classification Search ............. 623/1.1, 623/1.12, 1.15, 1.28, 1.31, 1.2
See application file for complete search history.

(56) References Cited

U.S. PATENT DOCUMENTS

| | | | |
|---|---|---|---|
| 5,514,154 A | 5/1996 | Lau et al. | |
| 5,681,346 A | 10/1997 | Orth et al. | |
| 6,019,789 A | 2/2000 | Dinh et al. | |
| 6,231,598 B1 | 5/2001 | Berry et al. | |
| 6,270,524 B1 | 8/2001 | Kim | |
| 6,613,081 B2 | 9/2003 | Kim et al. | |
| 6,673,107 B1 | 1/2004 | Brandt et al. | |
| 6,709,453 B2 | 3/2004 | Pinchasik et al. | |
| 6,863,684 B2 | 3/2005 | Kim et al. | |
| 6,896,696 B2 | 5/2005 | Doran et al. | |
| 6,896,697 B1 | 5/2005 | Yip | |
| 7,144,420 B2 | 12/2006 | Lenz | |
| 2003/0045925 A1 | 3/2003 | Jayaraman | |
| 2003/0125799 A1 | 7/2003 | Limon | |
| 2004/0073290 A1 | 4/2004 | Chouinard | |
| 2004/0073291 A1 | 4/2004 | Brown et al. | |
| 2004/0176837 A1* | 9/2004 | Atladottir et al. ............ | 623/1.35 |
| 2005/0182480 A1 | 8/2005 | Doran | |
| 2008/0262589 A1* | 10/2008 | Nagura ........................ | 623/1.2 |

FOREIGN PATENT DOCUMENTS

| | | | |
|---|---|---|---|
| DE | 297 16 476 U1 | 12/1997 | |
| EP | 0732088 A2 | 9/1996 | |
| WO | WO 0028922 A1 * | 5/2000 | |
| WO | 00/49971 A1 | 8/2000 | |
| WO | WO2006020127 A | 2/2006 | |
| WO | WO2007095437 A1 | 8/2007 | |

* cited by examiner

*Primary Examiner* — Eduardo C Robert
*Assistant Examiner* — Joshua Levine
(74) *Attorney, Agent, or Firm* — Vidas, Arrett and Steinkraus

(57) ABSTRACT

A stent has adjacent circumferential rings of struts. Adjacent rings being connected by a plurality of connectors. The stent having a hybrid of peak to valley and peak to peak connectors.

20 Claims, 13 Drawing Sheets

US 8,211,163 B2

HYBRID SYMMETRICAL STENT DESIGNS

CROSS-REFERENCE TO RELATED APPLICATIONS

This application claims priority from U.S. Application No. 60/844,307, filed on Sep. 13, 2006, the entire content of which is hereby incorporated by reference.

STATEMENT REGARDING FEDERALLY SPONSORED RESEARCH

Not Applicable

BACKGROUND OF THE INVENTION

A stent is a medical device introduced to a body lumen and is well known in the art. Typically, a stent is implanted in a blood vessel at the site of a stenosis or aneurysm endoluminally, i.e. by so-called "minimally invasive techniques" in which the stent in a radially reduced configuration, optionally restrained in a radially compressed configuration by a sheath and/or catheter, is delivered by a stent delivery system or "introducer" to the site where it is required. The introducer may enter the body from an access location outside the body, such as through the patient's skin, or by a "cut down" technique in which the entry blood vessel is exposed by minor surgical means.

Stents, grafts, stent-grafts, vena cava filters, expandable frameworks, and similar implantable medical devices, collectively referred to hereinafter as stents, are radially expandable endoprostheses which are typically intravascular implants capable of being implanted transluminally and enlarged radially after being introduced percutaneously. Stents may be implanted in a variety of body lumens or vessels such as within the vascular system, urinary tracts, bile ducts, fallopian tubes, coronary vessels, secondary vessels, etc. They may be self-expanding, expanded by an internal radial force, such as when mounted on a balloon, or a combination of self-expanding and balloon expandable (hybrid expandable).

Stents may be created by methods including cutting or etching a design from a tubular stock, from a flat sheet which is cut or etched and which is subsequently rolled or from one or more interwoven wires or braids.

The art referred to and/or described above is not intended to constitute an admission that any patent, publication or other information referred to herein is "prior art" with respect to this invention. In addition, this section should not be construed to mean that a search has been made or that no other pertinent information as defined in 37 C.F.R. §1.56(a) exists.

All US patents and applications and all other published documents mentioned anywhere in this application are incorporated herein by reference in their entirety.

Without limiting the scope of the invention a brief summary of some of the claimed embodiments of the invention is set forth below. Additional details of the summarized embodiments of the invention and/or additional embodiments of the invention may be found in the Detailed Description of the Invention below.

BRIEF SUMMARY OF THE INVENTION

In at least one embodiment, the invention is directed to a stent comprising a plurality of circumferential rings and a plurality of connectors which are evenly spaced about the circumference of the stent, thereby providing a symmetrical stent design. In at least one embodiment, the stent is a hybrid of a plurality of peak to peak connectors and a plurality of peak to valley connectors. In at least one embodiment, the plurality of connectors is peak to valley connectors.

In some embodiments, each peak to valley connector has a bend. In some embodiments, each peak to valley connector is straight. In some embodiments, each peak to peak connector has a bend. In some embodiments, each peak to peak connector extends at an angle offset from the longitudinal axis of the stent, or circumferentially, from one circumferential ring to the adjacent circumferential ring. In some embodiments, each peak to peak connector extends substantially parallel to the longitudinal axis of the stent.

In at least one embodiment, the stent has a proximal section, a middle section and a distal section where each section has at least two circumferential rings. A plurality of peak to peak connector engage adjacent circumferential rings of the proximal section, adjacent circumferential rings of the distal section and engage the proximal section to the middle section and the middle section to the distal section. A plurality of peak to valley connectors, evenly spaced about the circumference of the stent, engages adjacent circumferential rings of the middle section.

These and other embodiments which characterize the invention are pointed out with particularity in the claims annexed hereto and forming a part hereof. However, for further understanding of the invention, its advantages and objectives obtained by its use, reference can be made to the drawings which form a further part hereof and the accompanying descriptive matter, in which there is illustrated and described an embodiments of the invention.

BRIEF DESCRIPTION OF THE SEVERAL VIEWS OF THE DRAWING(S)

A detailed description of the invention is hereafter described with specific reference being made to the drawings.

DETAILED DESCRIPTION OF THE INVENTION

Figure 1:
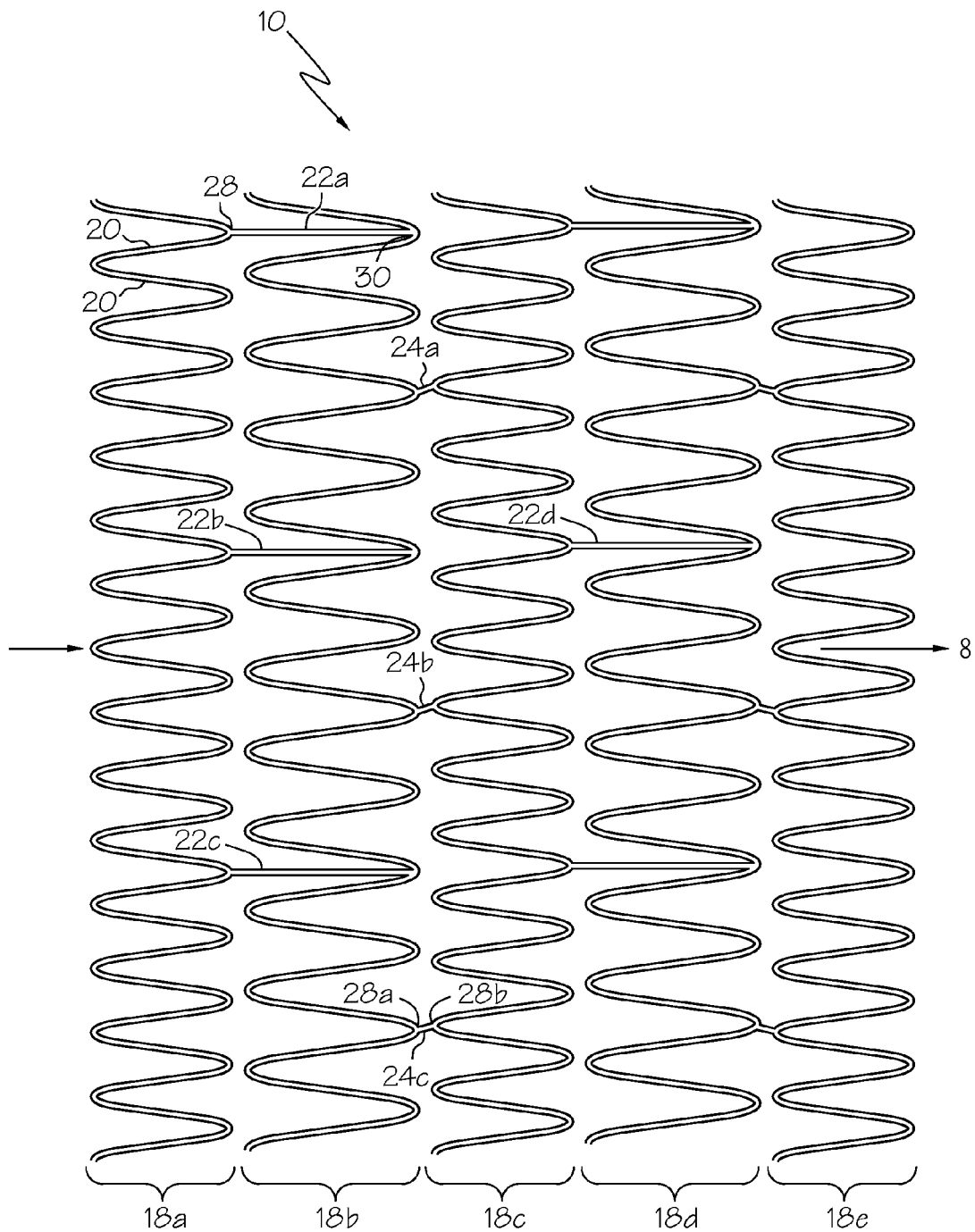
FIG. 1 is a rolled out view of an embodiment of the invention.

While this invention may be embodied in many different forms, there are described in detail herein specific embodiments of the invention. This description is an exemplification of the principles of the invention and is not intended to limit the invention to the particular embodiments illustrated.

For the purposes of this disclosure, like reference numerals in the figures shall refer to like features unless otherwise indicated.

In FIG. 1 an embodiment of the invention is shown and comprises a stent 10, which is shown in a flat pattern or rolled out configuration. The stent 10 is provided with both peak to valley connectors 22 and peak to peak connectors 24. In this embodiment, the peak to valley connectors 22 and the peak to peak connectors 24 alternate along the longitudinal axis 8 of the stent 10. Thus, this stent 10 is a hybrid of peak to valley connectors 22 and peak to peak connectors 24. The stent 10 is comprised of a plurality of struts 20 which form circumferential rings 18. For purposes of illustration the embodiments, shown in FIGS. 1-11 have 5 or 7 circumferential rings 18. It is within the scope of the invention for a stent 10 to have any number of circumferential rings 18 desired depending on the length of the stent 10 needed for a particular anatomy. Note that the stent 10 in FIG. 12 has sixteen (16) circumferential rings 18 and the stent 10 in FIG. 13 has fifteen (15) circumferential rings 18.

For descriptive purposes, in another aspect of the invention, adjacent circumferential rings 18 may be considered to form ring pairs. Thus, if a stent 10 has three circumferential rings 18, the first and second circumferential rings 18 form a ring pair, and similarly, the second and third circumferential rings 18 form a ring pair, etc.

In at least one embodiment, the struts 20 of adjacent circumferential rings 18 of have a first length and a second length where the first and second lengths are different. This is illustrated, for example, in FIG. 1 where the struts 20 of the first circumferential ring 18a have a first length and the struts 20 of the second circumferential ring 18b have a second length and the first length is shorter than the second length. Thus, the lengths of the struts 20 in adjacent circumferential rings 18 alternate between a first length and a second length. In at least one embodiment, the struts 20 of adjacent circumferential rings 18 have the same length. In at least one embodiment struts 20 which make up a given ring 18 include struts of different lengths.

Adjacent circumferential rings 18 are engaged by at least one connector 22,24. The connectors 22,24 may extend longitudinally, like the peak to valley connectors 22 of FIG. 1 or the connectors 22,24 may extend in a circumferential direction in the manner of the peak to peak connectors 24 of FIG. 1. In some embodiments the connectors 22,24 are straight, include at least one bend and/or include other shapes and configurations.

Note that the connectors 22,24 in the stent designs in FIGS. 1-13 are evenly spaced about the circumference of the stent 10 thereby providing a symmetrical stent design. Some embodiments of the invention can be provided with non-symmetrical spacing of connectors, such as for example to provide for side branch axis at a vessel bifurcation, etc.

In the embodiments shown connectors 22,24 have the same number of struts 20 between the same end. Thus, as illustrated in FIG. 1, there are eight struts 20, or four strut pairs, between the first ends of each peak to peak connector 24. Similarly, the second ends of each peak to peak connector 24 have ten struts 20, or five strut pairs, between them.

Although the stent 10 in FIG. 1 has three connectors 22,24 between adjacent circumferential rings 18, it is within the scope of the invention for there to be two, three, four, five, six, seven, eight, nine, ten or more connectors 22,24 between adjacent circumferential rings 18. In some embodiments the connectors 22,24 are evenly spaced about the circumference of the stent. The embodiments illustrated, for example, in FIGS. 3-6 have two evenly spaced connectors 22,24 engaging adjacent circumferential rings 18.

In FIG. 1, the stent 10 has five circumferential rings 18a-e. Peak to valley connectors 22 engage the first circumferential ring 18a to the second circumferential ring 18b, as well as the third circumferential ring 18c to the fourth circumferential ring 18d. A peak to valley connector 22 engages the peak 28 of one circumferential ring 18 to a valley 30 on the adjacent circumferential ring 18. In this embodiment there are three peak to valley connectors 22 about the circumference of the stent 10, for a total of six peak to valley connectors 22. The peaks 28, to which the first ends of each peak to valley connector 22 are engaged, have ten struts 20, or five strut pairs, between them. Thus, in the first circumferential ring 18a there are ten struts 20 between peak to valley connector 22a and peak to valley connector 22b as well as between peak to valley connector 22b and peak to valley connector 22c. The valleys 30, to which the second ends of each peak to valley connector 22 are engaged, have eight struts 20, or four strut pairs, between them. Thus, in the second circumferential ring 18b, there are eight struts 20 between peak to valley connector 22a and peak to valley connector 22b as well as between peak to valley connector 22b and peak to valley connector 22c.

Peak to peak connectors 24 engage the second circumferential ring 18b to the third circumferential ring 18c, as well as the fourth circumferential ring 18d to the fifth circumferential ring 18e. A peak to peak connector 24 engages the peak 28a of one circumferential ring 18 to a peak 28b of the adjacent circumferential ring 18. In this embodiment, between adjacent circumferential rings 18, there are three peak to peak connectors 24 about the circumference of the stent 10, so that the stent 10 has a total of six peak to peak connectors 24. The peaks 28, to which the first ends of each peak to peak connector 24 are engaged, have eight struts 20, or four strut pairs, between them. Thus, in the second circumferential ring 18b, there are eight struts 20 between peak to peak connector 24a and peak to peak connector 24b as well as between peak to peak connector 24b and peak to peak connector 24c. The peaks 28, to which the second ends of each peak to peak connector 24 are engaged, have ten struts 20, or five strut pairs, between them. Thus, in the third circumferential ring 18c, there are ten struts 20 between peak to peak connector 24a and peak to peak connector 24b as well as between peak to peak connector 24b and peak to peak connector 24c.

The peak to valley connectors 22 each have a second end which is engaged to a valley 30 of a circumferential ring 18. Four struts 20, or two struts pairs separate the second end of a peak to valley connector 22 from the first end of a peak to peak connector 24, shown for example, between peak to valley connector 22a and peak to peak connector 24a of FIG. 1. The peak to peak connectors 24 each have a second end engaged to a peak 28 of a circumferential ring 18. Five struts 20 separate the second end of the peak to peak connector 24 from the first end of a peak to valley connector 22, shown for example between peak to peak connector 24a and peak to valley connector 22d.

Figure 2:
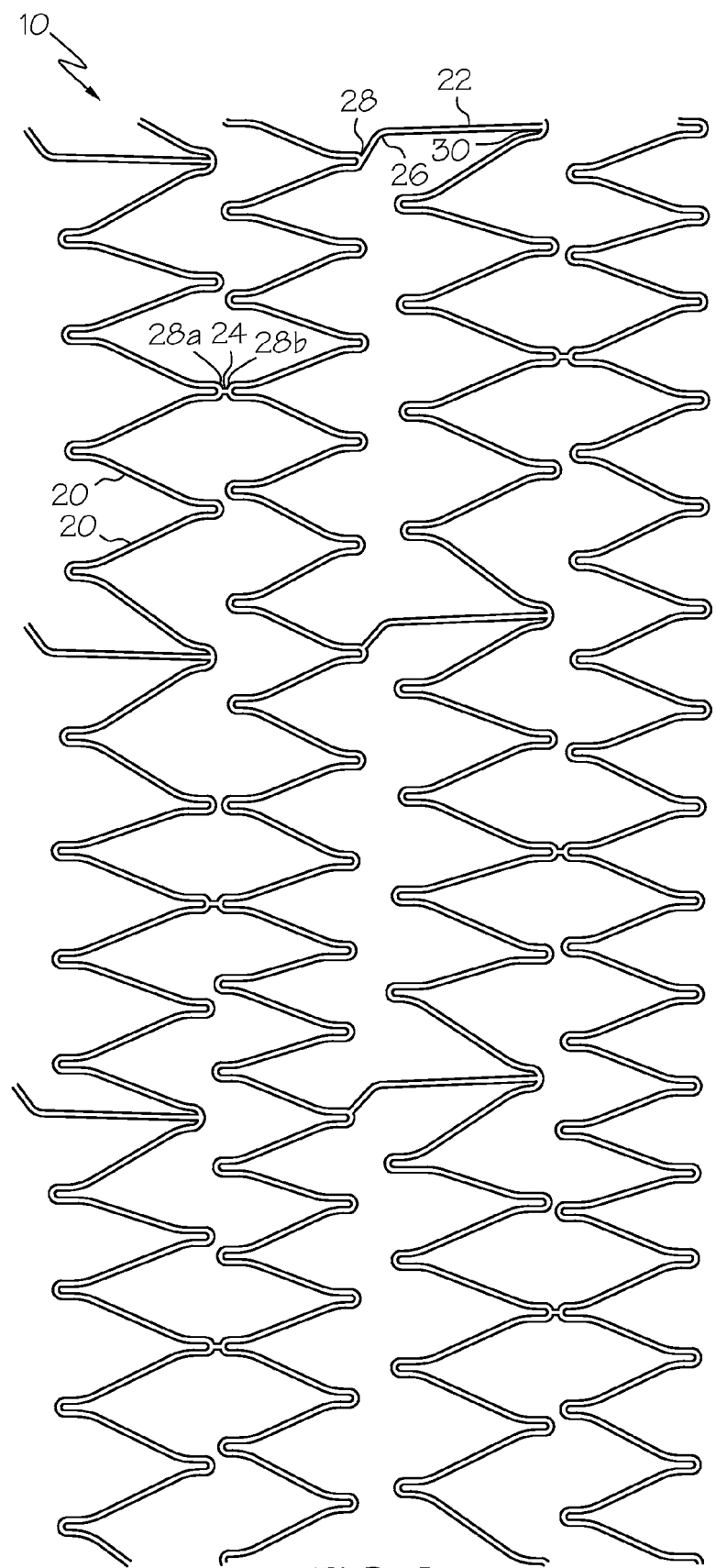
FIG. 2 is a rolled out view of an embodiment of the invention.

FIG. 2 is an alternative embodiment of the stent 10 in FIG. 1. In this embodiment, the peak to valley connectors 22 have a bend 26 and the peak to peak connectors 24 are straight, extending longitudinally from a peak 28a on a circumferential ring 18 to a peak 28b on the adjacent circumferential ring 18. Although the other stent embodiments illustrated in FIGS. 3-12 have straight peak to valley connectors 22, it is within the scope of the invention for those stent embodiments to have peak to valley connectors 22 with a bend 26, as shown in FIG. 2, instead of straight peak to valley connectors 22.

In FIGS. 1 and 2, peak to valley connectors 22 engage the first circumferential ring 18a to the second circumferential ring 18b. In at least one embodiment, peak to valley connectors 22 engage the second circumferential ring 18b to the third circumferential ring 18c as well as the fourth circumferential ring 18d to the fifth circumferential ring 18e while peak to peak connectors 24 engage the first circumferential ring 18a to the second circumferential ring 18b as well as the third circumferential ring 18c to the fourth circumferential ring 18d.

In at least one embodiment, the stent 10 comprises circumferential rings 18 of struts 20 and circumferential rings 18 of connectors 22,24 which alternate, e.g. circumferential ring 18 of struts 20—circumferential ring 18 of connectors 22,24—circumferential ring of struts 20, etc. The circumferential rings 18 of connectors 22,24 alternate between circumferential rings 18 of peak to valley connectors 22 and circumferential rings 18 of peak to peak connectors 24, with the first circumferential rings 18 of connectors 22,24 being either peak to valley connectors 22, as shown in FIGS. 1 and 2, or peak to peak connectors 24. The first ends of the connectors 22,24 within a circumferential ring 18 of connectors 22,24 are separated by an equal number of struts, as illustrated in FIG. 1 for example.

Figure 3:
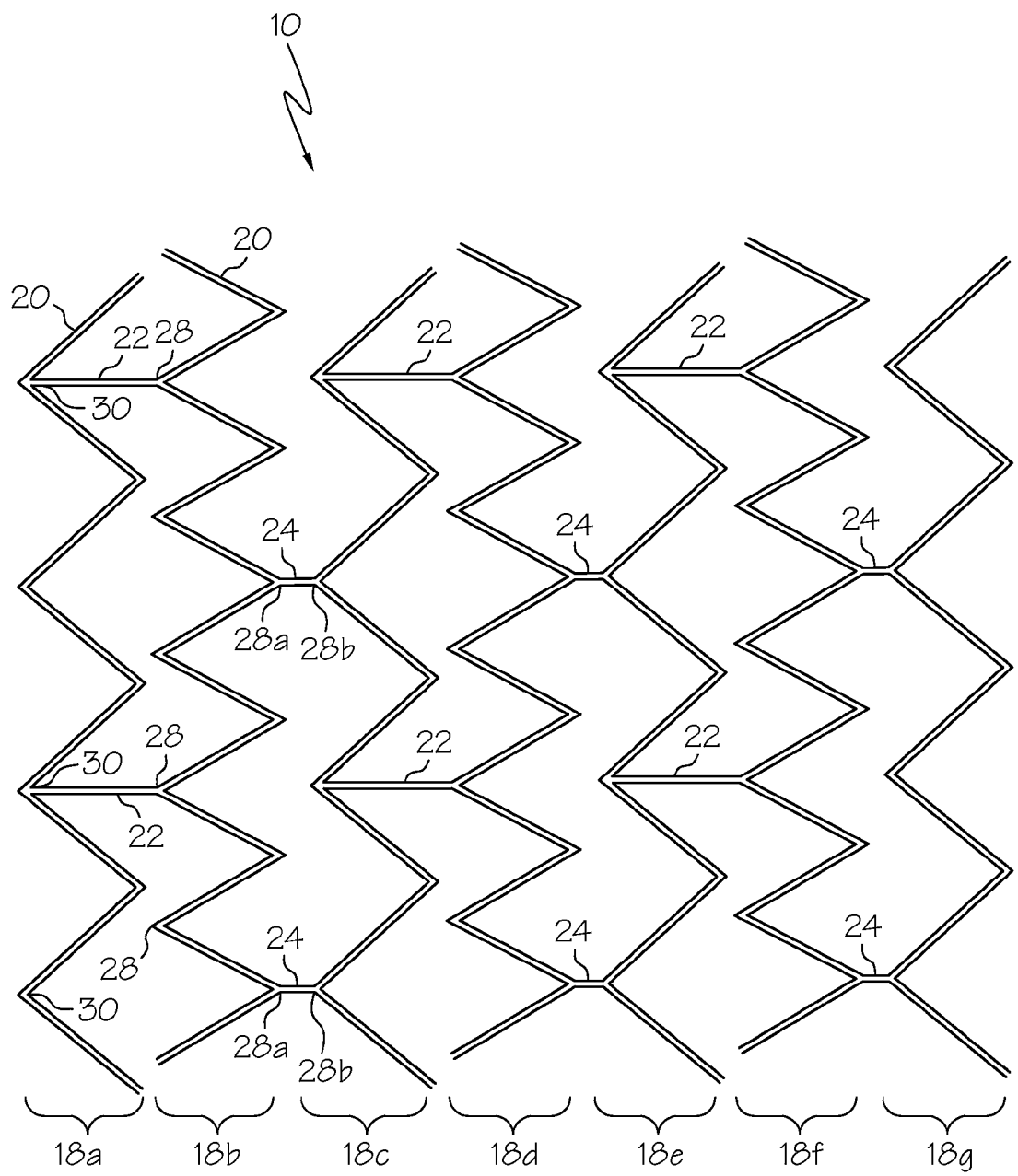
FIG. 3 is a rolled out view of an embodiment of the invention.

FIG. 3 depicts yet another embodiment of the invention, wherein the stent 10 is provided with at least a plurality of circumferential rings 18a-g. Peak to valley connectors 22 engage the first circumferential ring 18a to the second circumferential ring 18b, the third circumferential ring 18c to the fourth circumferential ring 18d, and the fifth circumferential ring 18e to the sixth circumferential ring 18f. Four struts 20, or two strut pairs, separate the first ends of the peak to valley connectors 22 that are engaged to the valleys 30 of the circumferential ring 18a,c,e. Six struts 20, or three strut pairs, separate the second ends of the peak to valley connectors 22 that are engaged to the peaks 28 of the circumferential ring 18b,d,f. Peak to peak connectors 24 engage the second circumferential ring 18b to the third circumferential ring 18c, the fourth circumferential ring 18d to the fifth circumferential ring 18e and the sixth circumferential ring 18f to the seventh circumferential ring 18g. Six struts 20, or three strut pairs, separate the first ends of the peak to peak connectors 24 engaged to the peaks 28a of the circumferential ring 18b,d,f. Four struts 20, or two strut pairs, separate the second ends of the peak to peak connectors 24 engaged to the peaks 28b of the circumferential rings 18c,e,g. In this embodiment, three struts 20 separate the second ends of the peak to valley connectors 22 from the first ends of the peak to peak connectors 24 and two struts 20 separate the second ends of the peak to peak connectors 24 from the first ends of the peak to valley connectors 22.

Though the various embodiments depicted in FIGS. 3-13 may have a variety of different connector configurations (e.g. longitudinally oriented, circumferentially oriented or angled, straight, bent, etc.). In the embodiments shown, at least the peak to peak connectors 24 are substantially parallel to the longitudinal axis of the stent.

Figure 4:
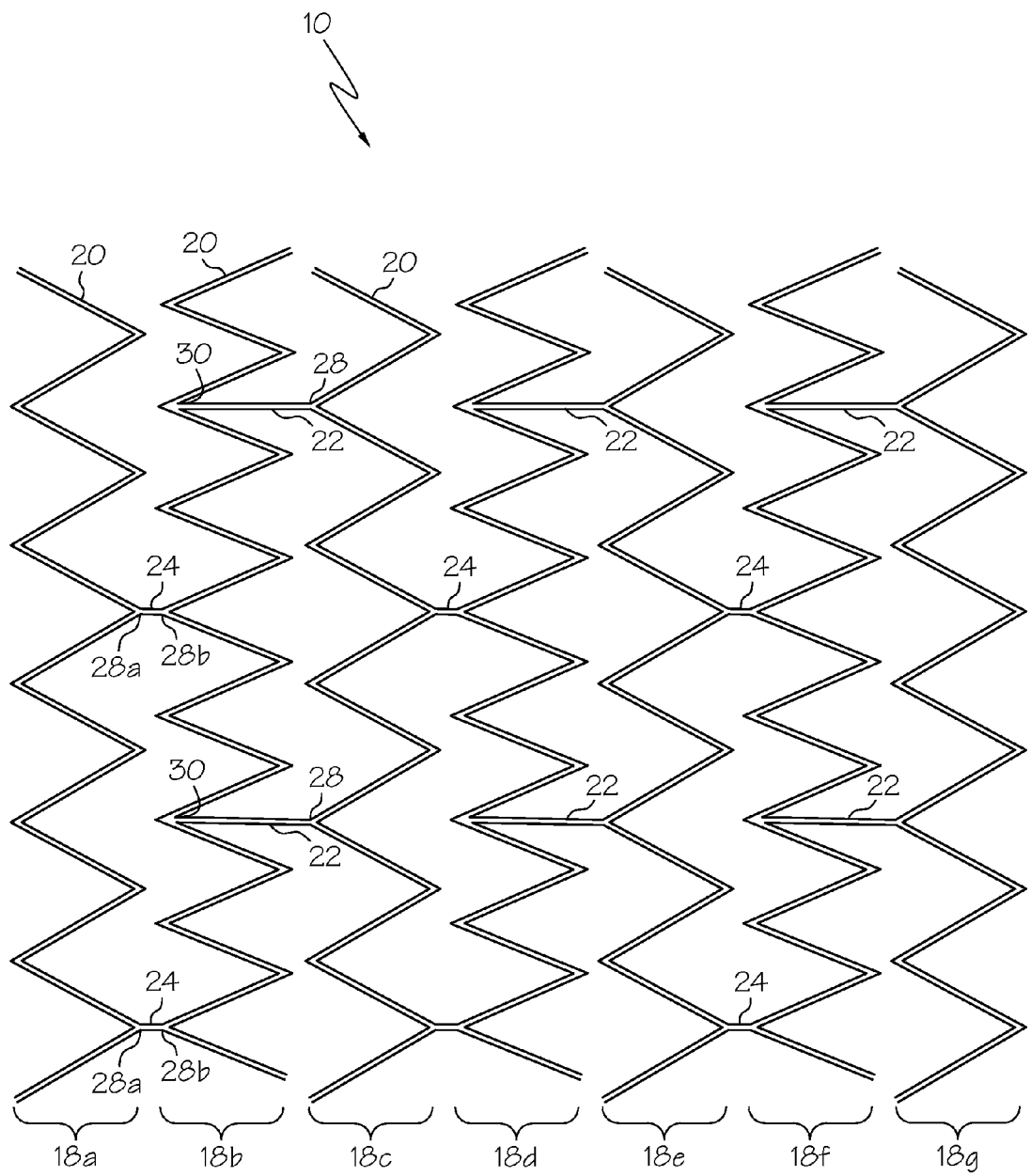
FIG. 4 is a rolled out view of an embodiment of the invention.

The stent 10 of FIG. 4 also is shown with seven circumferential rings 18a,b,c,d,e,f,g, In this embodiment, peak to peak connectors 24 engage the first circumferential ring 18a to the second circumferential ring 18b, the third circumferential ring to the fourth circumferential ring, and the fifth circumferential ring 18e to the sixth circumferential ring 18f. Six struts 20, or three strut pairs, separate the first ends of the peak to peak connectors 24 that are engaged to the peaks 28a of the circumferential rings 18a,c,e. Eight struts 20, or four strut pairs, separate the second ends of the peak to peak connectors 24 that are engaged to the peaks 28b of the circumferential rings 18b,d,f. Peak to valley connectors 22 engage the second circumferential ring 18b to the third circumferential ring 18c, the fourth circumferential ring 18d to the fifth circumferential ring 18e, and the sixth circumferential ring 18f to the seventh circumferential ring 18g. Eight struts 20, or four strut pairs, separate the first ends of the peak to valley connectors 22 engaged to the valleys 30 of the circumferential rings 18b,d,f. Six struts 20, or three strut pairs, separate the second ends of the peak to valley connectors 22 engaged to the peaks 28 of the circumferential rings 18c,e,g. In this embodiment, four struts 20, or two strut pairs, separate the second ends of the peak to peak connectors 24 from the first ends of the peak to valley connectors 22 and three struts 20 separate the second ends of the peak to valley connectors 22 from the first ends of the peak to peak connectors 24.

Figure 5:
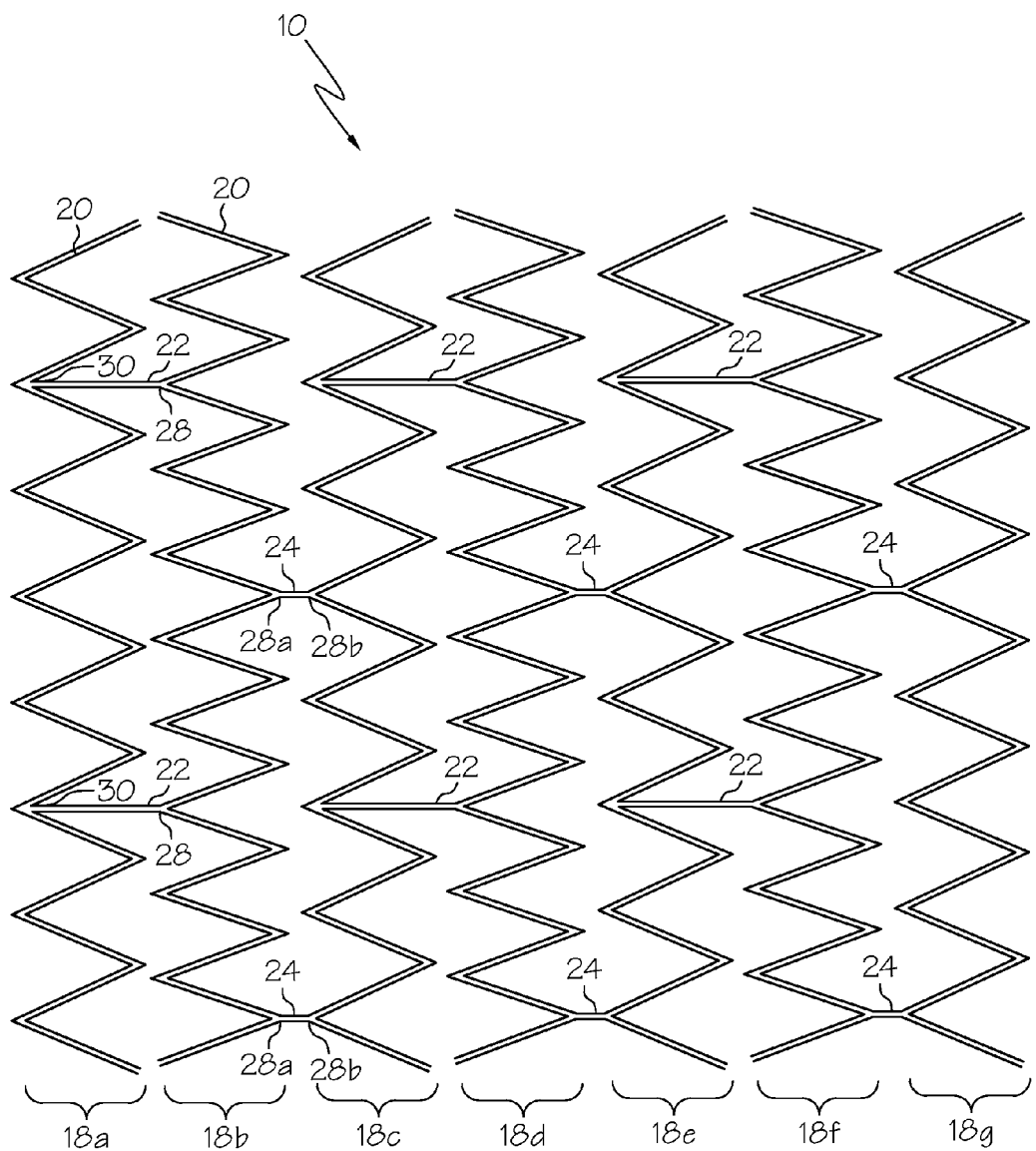
FIG. 5 is a rolled out view of an embodiment of the invention.

The stent 10 in FIG. 5 has peak to valley connectors 22 engaging the first circumferential ring 18a to the second circumferential ring 18b, the third circumferential ring 18c to the fourth circumferential ring 18d, and the fifth circumferential ring 18e to the sixth circumferential ring 18f. Eight struts 20, or four strut pairs, separate the first ends of the peak to valley connectors 22 engaged to the valleys 30 of the circumferential rings 18a,c,e. Ten struts 20, or five strut pairs, separate the second ends of the peak to valley connectors 22 engaged to the peaks 28 of the circumferential rings 18b,e,f. Peak to peak connectors 24 engage the second circumferential ring 18b to the third circumferential ring 18c, the fourth circumferential ring 18d and the fifth circumferential ring 18e, and the sixth circumferential ring 18f and the seventh circumferential ring 18g. Ten struts 20, or five strut pairs, separate the first ends of the peak to peak connectors 24 that are engaged to the peaks 28a of the circumferential rings 18b,d,f. Eight struts 20, or four strut pairs, separate the second ends of the peak to peak connectors 24 that are engaged to the peaks 28b of the circumferential rings 18c,e,g. In this embodiment, five struts 20 separate the second ends of the peak to valley connectors 22 from the first ends of the peak to peak connectors 24 and four struts 20, or two strut pairs, separate the second ends of the peak to peak connectors 24 from the first ends of the peak to valley connectors 22.

Figure 6:
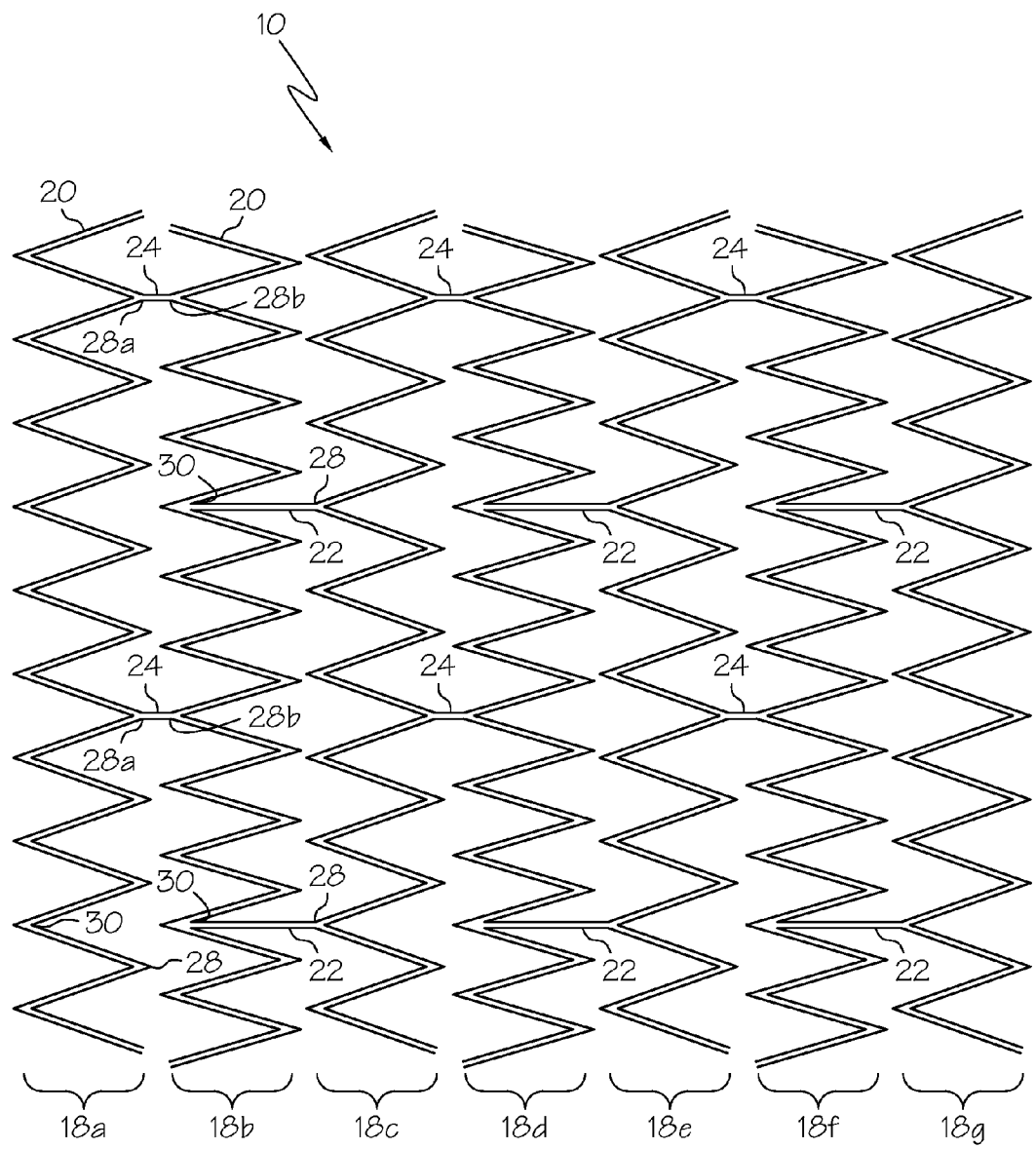
FIG. 6 is a rolled out view of an embodiment of the invention.

The stent 10 in FIG. 6 has peak to peak connectors 24 engaging the first circumferential ring 18a to the second circumferential ring 18b, the third circumferential ring 18c to the fourth circumferential ring 18d, the fifth circumferential ring 18e to the sixth circumferential ring 18f. Ten struts 20, or five strut pairs, separate the first ends of the peak to peak connectors 24 engaged to the peaks 28a of the circumferential rings 18a,c,e. Twelve struts 20, or six strut pairs, separate the second ends of the peak to peak connectors 24 engaged to the peaks 28b of the circumferential rings 18b,d,f. Peak to valley connectors 22 engage the second circumferential ring 18b to the third circumferential ring 18c, the fourth circumferential ring 18d to the fifth circumferential ring 18e, and the sixth circumferential ring 18f to the seventh circumferential ring 18g. Twelve struts 20, or six strut pairs, separate the first ends of the peak to valley connectors 22 engaged to the valleys 30 of circumferential rings 18b,d,f. Ten struts 20, or five strut pairs, separate the second ends of the peak to valley connectors 22 engaged to the peaks 28 of circumferential rings 18c,e,g. In this embodiment, six struts 20, or three strut pairs, separate the second ends of the peak to peak connectors 24 from the first ends of the peak to valley connectors 22 and five struts separate the second ends of the peak to valley connectors 22 from the first ends of the peak to peak connectors 24.

Figure 7:
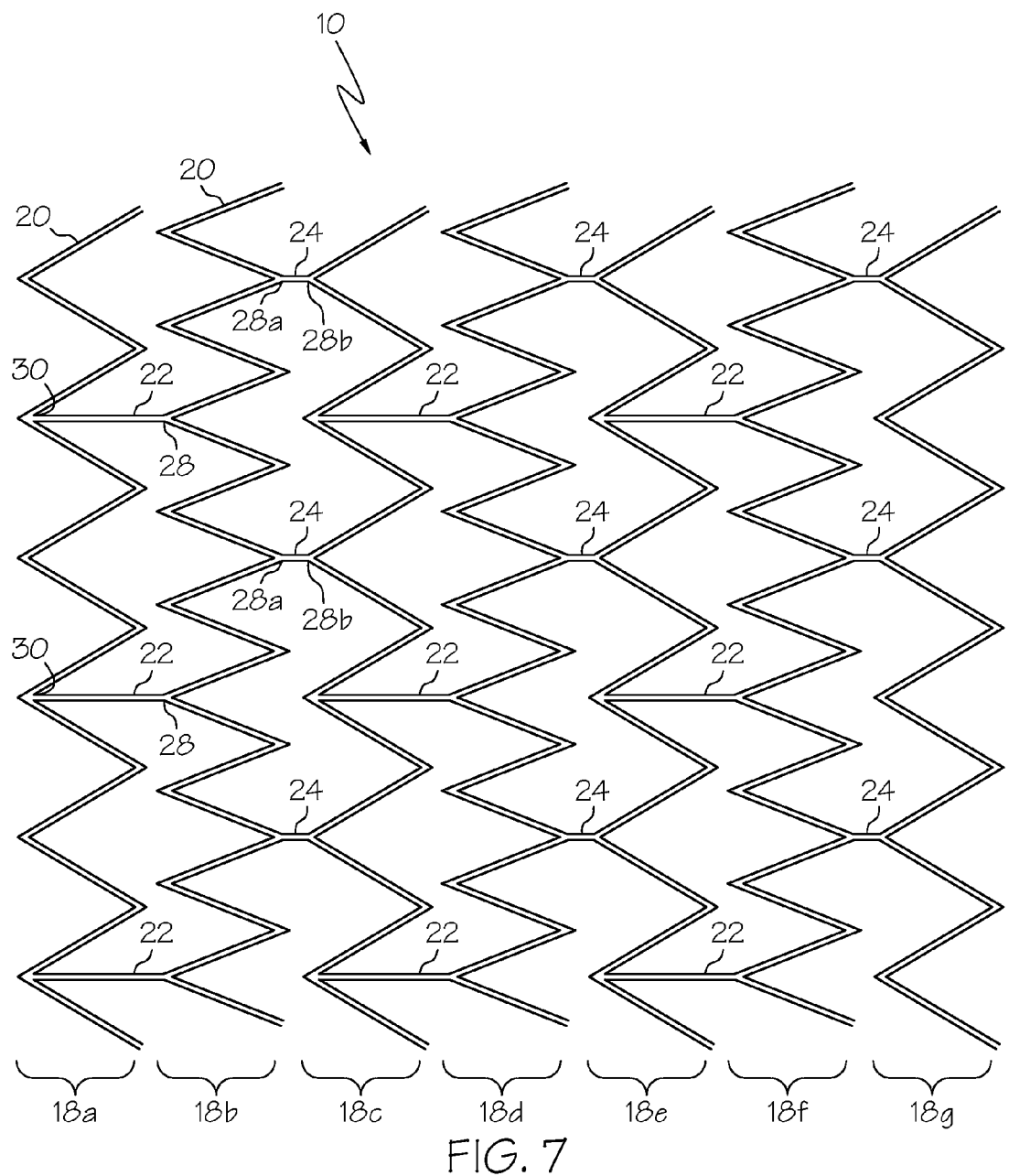
FIG. 7 is a rolled out view of an embodiment of the invention.

In FIG. 7, the stent 10 has peak to valley connectors 22 engaging the first circumferential ring 18a to the second circumferential ring 18b, the third circumferential ring 18c to the fourth circumferential ring 18d, and the fifth circumferential ring 18e to the sixth circumferential ring 18f. Four struts 20, or two strut pairs, separate the first ends of the peak to valley connectors 22 engaged to the valleys 30 of the circumferential rings 18a,c,e. Six struts 20, or three strut pairs, separate the second ends of the peak to valley connectors 22 engaged to the peaks 28 of the circumferential rings 18b,d,f. Peak to peak connectors 24 engage the second circumferential ring 18b to the third circumferential ring 18c, the fourth circumferential ring 18d to the fifth circumferential ring 18e and the sixth circumferential ring 18f to the seventh circumferential ring 18g. Six struts 20, or three strut pairs, separate the first ends of the peak to peak connectors 24 engaged to the peaks 28a of circumferential rings 18b,d,f. Four struts 20, or two strut pairs, separate the second ends of the peak to peak connectors 24 engaged to the peaks 28b of circumferential rings 18c,e,g. In this embodiment, three struts 20 separate the second ends of the peak to valley connectors 22 from the first ends of the peak to peak connectors 24 and two struts 20, or one strut pair, separate the second ends of the peak to peak connectors 24 from the first ends of the peak to valley connectors 22.

Figure 8:
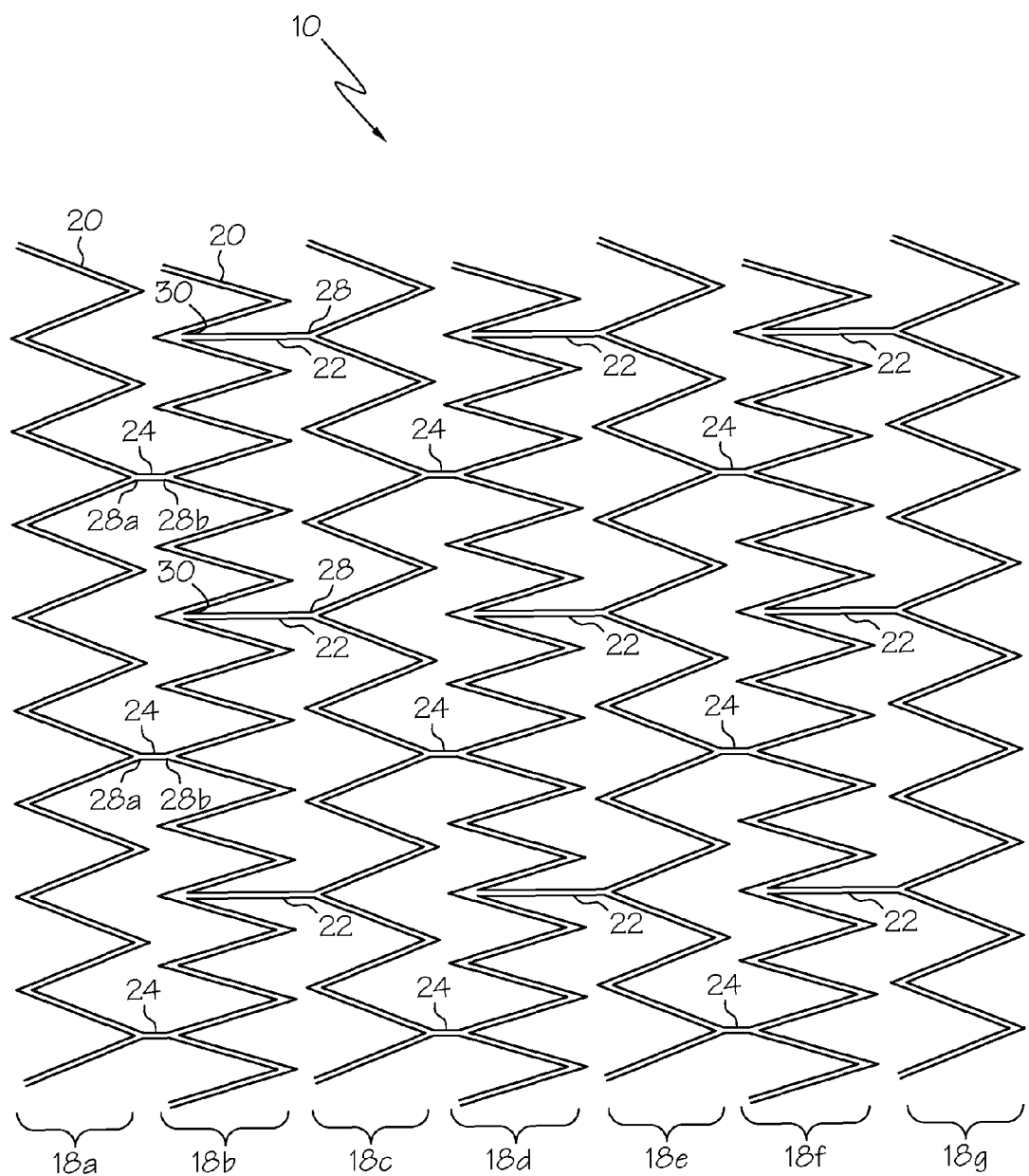
FIG. 8 is a rolled out view of an embodiment of the invention.

The stent in FIG. 8 has peak to peak connectors 24 engaging the first circumferential ring 18a to the second circumferential ring 18b, the third circumferential ring 18c to the fourth circumferential ring 18d, and the fifth circumferential ring 18e to the sixth circumferential ring 18f. Six struts 20, or three strut pairs, separate the first ends of the peak to peak connectors 24 engaged to the peaks 28a of circumferential rings 18a,c,e. Eight struts 20, or four strut pairs, separate the second ends of the peak to peak connectors 24 engaged to the peaks 28b of circumferential rings 18b,d,f. Peak to valley connectors 22 engage the second circumferential ring 18b to the third circumferential ring 18c, the fourth circumferential ring 18d to the fifth circumferential ring 18e and the sixth circumferential ring 18f to the seventh circumferential ring 18g. Eight struts 20, or four strut pairs, separate the first ends of the peak to valley connectors 22 engaged to the valleys 30 of circumferential rings 18b,d,f. Six struts 20, or three strut pairs, separate the second ends of the peak to valley connectors 22 engaged to the peaks 28 of circumferential rings 18c,e,g. In this embodiment, four struts 20, or two strut pairs, separate the second ends of the peak to peak connectors 24 from the first ends of the peak to valley connectors 22 and three struts separate the second ends of the peak to valley connectors 22 from the first ends of the peak to peak connectors 24.

Figure 9:
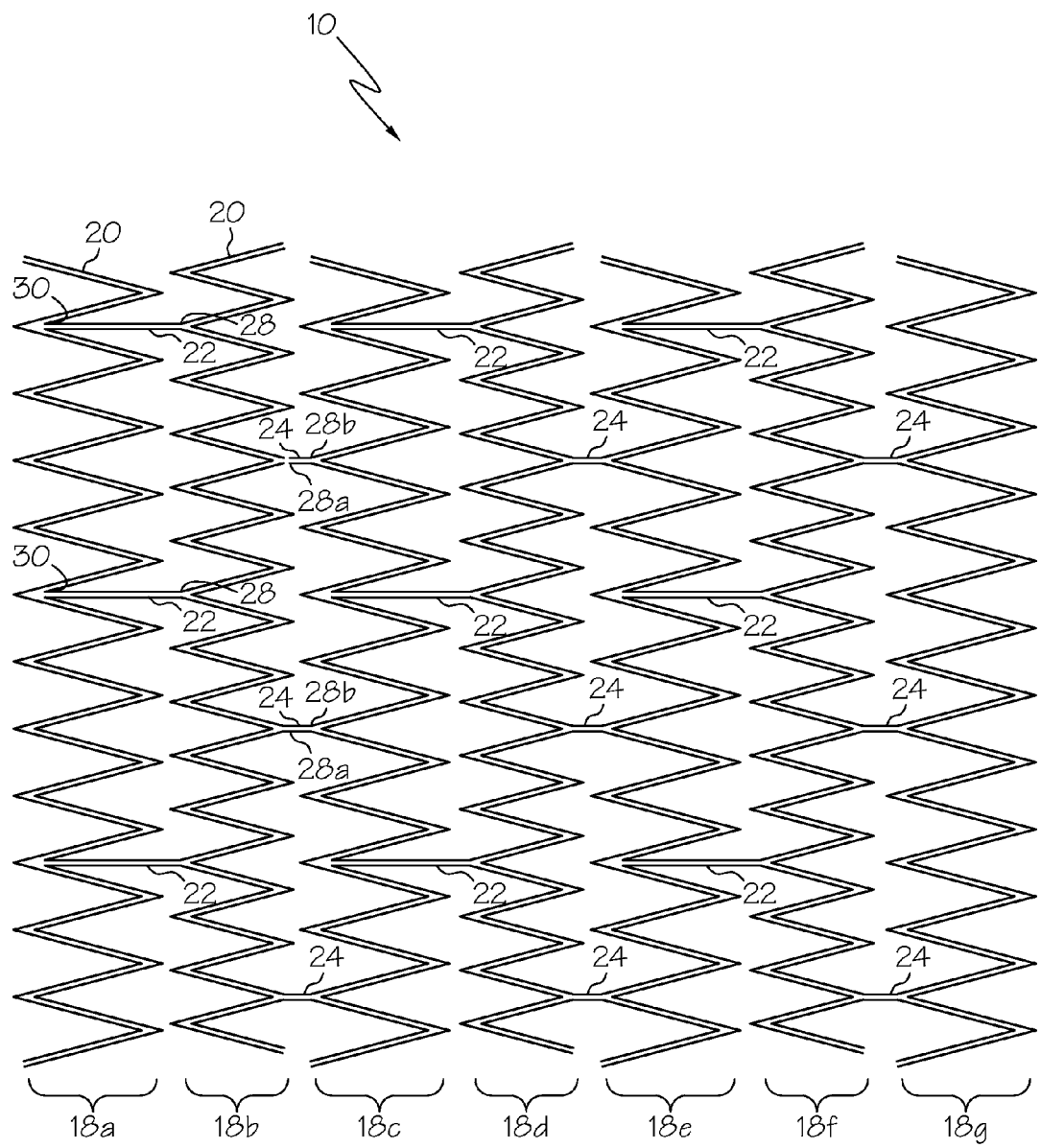
FIG. 9 is a rolled out view of an embodiment of the invention.

In FIG. 9, peak to valley connectors 22 engage the first circumferential ring 18a to the second circumferential ring 18b, the third circumferential ring 18c to the fourth circumferential ring 18d and the fifth circumferential ring 18e to the sixth circumferential ring 18f. Eight struts 20, or four strut pairs, separate the first ends of the peak to valley connectors 22 engaged to the valleys 30 of circumferential rings 18a,c,e. Ten struts 10, or five strut pairs, separate the second ends of the peak to valley connectors 22 engaged to the peaks 28 of circumferential rings 18b,d,f. Longitudinally oriented peak to peak connectors 24 engage the second circumferential ring 18b to the third circumferential ring 18c, the fourth circumferential ring 18d to the fifth circumferential ring 18e and the sixth circumferential ring 18f to the seventh circumferential ring 18g. Ten struts 20, or five strut pairs, separate the first ends of the peak to peak connectors 24 engaged to the peaks 28a of circumferential rings 18b,d,f. Eight struts 20, or four strut pairs, separate the second ends of the peak to peak connectors 24 engaged to the peaks 28b of circumferential rings 18c,e,g. In this embodiment, five struts 20 separate the second ends of the peak to valley connectors 22 from the first ends of the peak to peak connectors 24 and four struts 20, or two strut pairs, separate the second ends of the peak to peak connectors 24 from the first ends of the peak to valley connectors 22.

Figure 10:
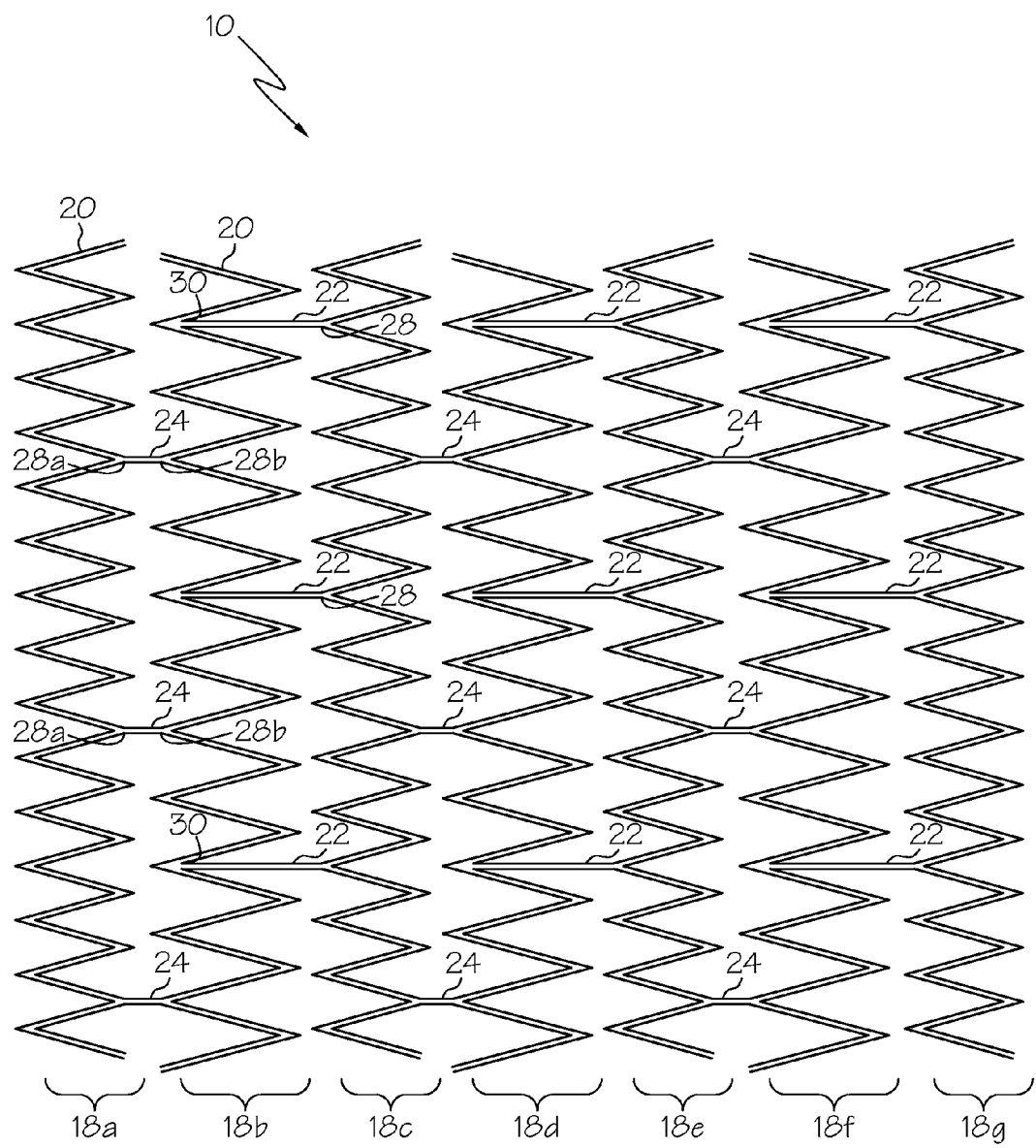
FIG. 10 is a rolled out view of an embodiment of the invention.

The stent 10 of FIG. 10, has peak to peak connectors 24 engaging the first circumferential ring 18a to the second circumferential ring 18b, the third circumferential ring 18c to the fourth circumferential ring 18d, and the fifth circumferential ring 18e to the sixth circumferential ring 18f. Ten struts 20, or five strut pairs, separate the first ends of the peak to peak connectors 24 engaged to the peaks 28a of circumferential rings 18a,c,e. Eight struts 20, or four strut pairs, separate the second ends of the peak to peak connectors 24 engaged to the peaks 28b of circumferential rings 18b,d,f. Peak to valley connectors 22 engage the second circumferential ring 18b to the third circumferential ring 18c, the fourth circumferential ring 18d to the fifth circumferential ring 18e, and the sixth circumferential ring 18f to the seventh circumferential ring 18g. Eight struts 20, or four strut pairs, separate the first ends of the peak to valley connectors 22 engaged to the valleys 30 of circumferential rings 18b,d,f. Ten struts 20, or five strut pairs, separate the second ends of the peak to valley connectors 22 engaged to the peaks 28 of circumferential rings 18c,e,g. In this embodiment, four struts 20, or two strut pairs, separate the second ends of the peak to peak connectors 24 from the first ends of the peak to valley connectors 22 and five struts 20 separate the second ends of the peak to valley connectors 22 from the first ends of the peak to peak connectors 24.

Figure 11:
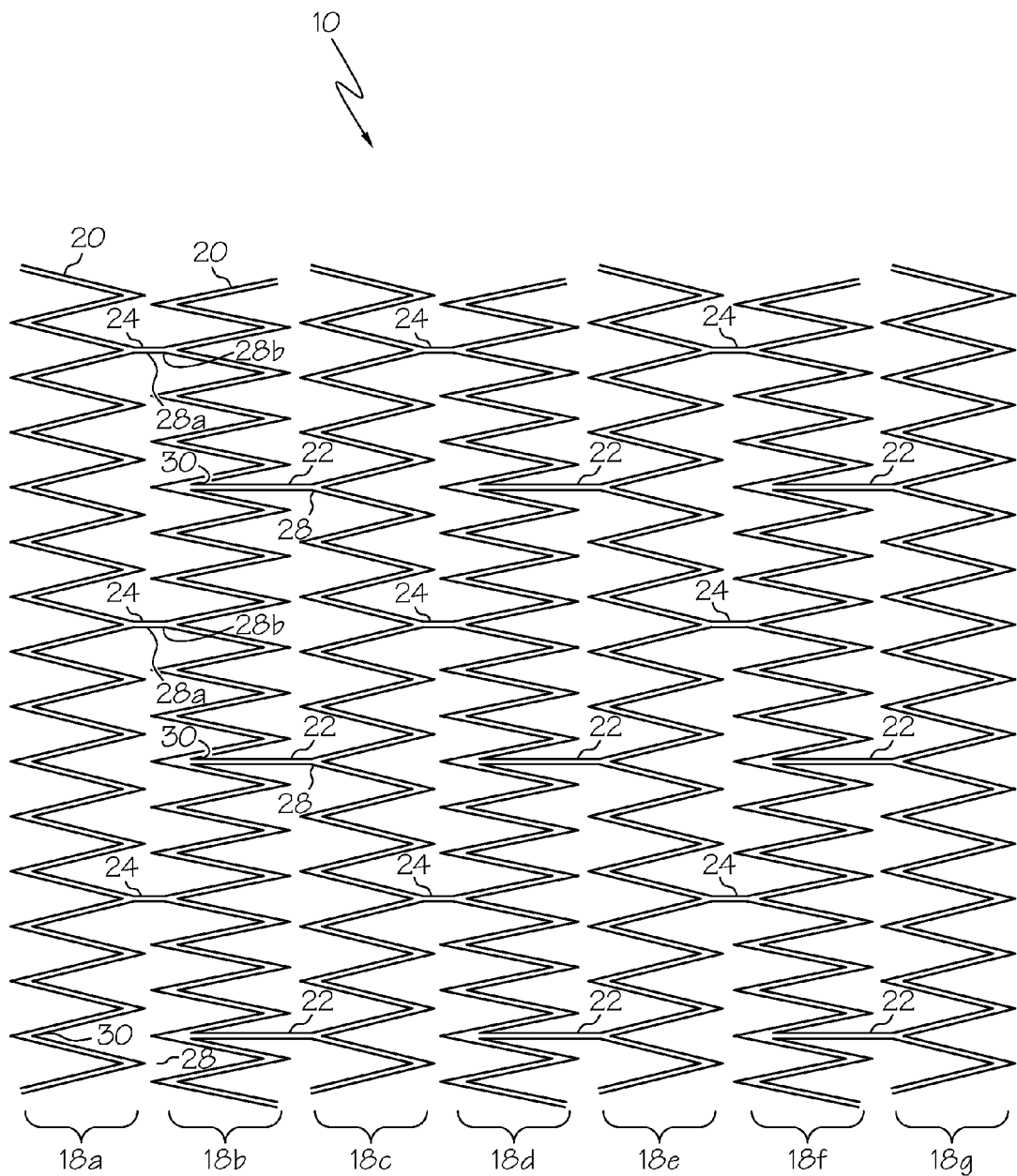
FIG. 11 is a rolled out view of an embodiment of the invention.

In FIG. 11, peak to peak connectors 24 engage the first circumferential ring 18a to the second circumferential ring 18b, the third circumferential ring 18c to the fourth circumferential ring 18d and the fifth circumferential ring to the sixth circumferential ring 18f. Ten struts 20, or five strut pairs, separate the first ends of the peak to peak connectors 24 engaged to the peaks 28a of circumferential rings 18a,c,e. Twelve struts 20, or six strut pairs, separate the second ends of the peak to peak connectors 24 engaged to the peaks 28b of circumferential rings 18b,d,f. Peak to valley connectors 22 engage the second circumferential ring 18b to the third circumferential ring 18c, the fourth circumferential ring 18d to the fifth circumferential ring 18e and the sixth circumferential ring 18f to the seventh circumferential ring 18g. Twelve struts 20, or six strut pairs, separate the first ends of the peak to valley connectors 22 engaged to the valleys 30 of circumferential rings 18b,d,f. Ten struts 20, or five strut pairs, separate the second ends of the peak to valley connectors 22 engaged to circumferential rings 18c,e,g. In this embodiment, six struts 20, or three strut pairs, separate the second ends of the peak to peak connectors 24 from the first ends of the peak to valley connectors 22 and five struts 20 separate the second ends of the peak to valley connectors 22 from the first ends of the peak to peak connectors 24.

Figure 12:
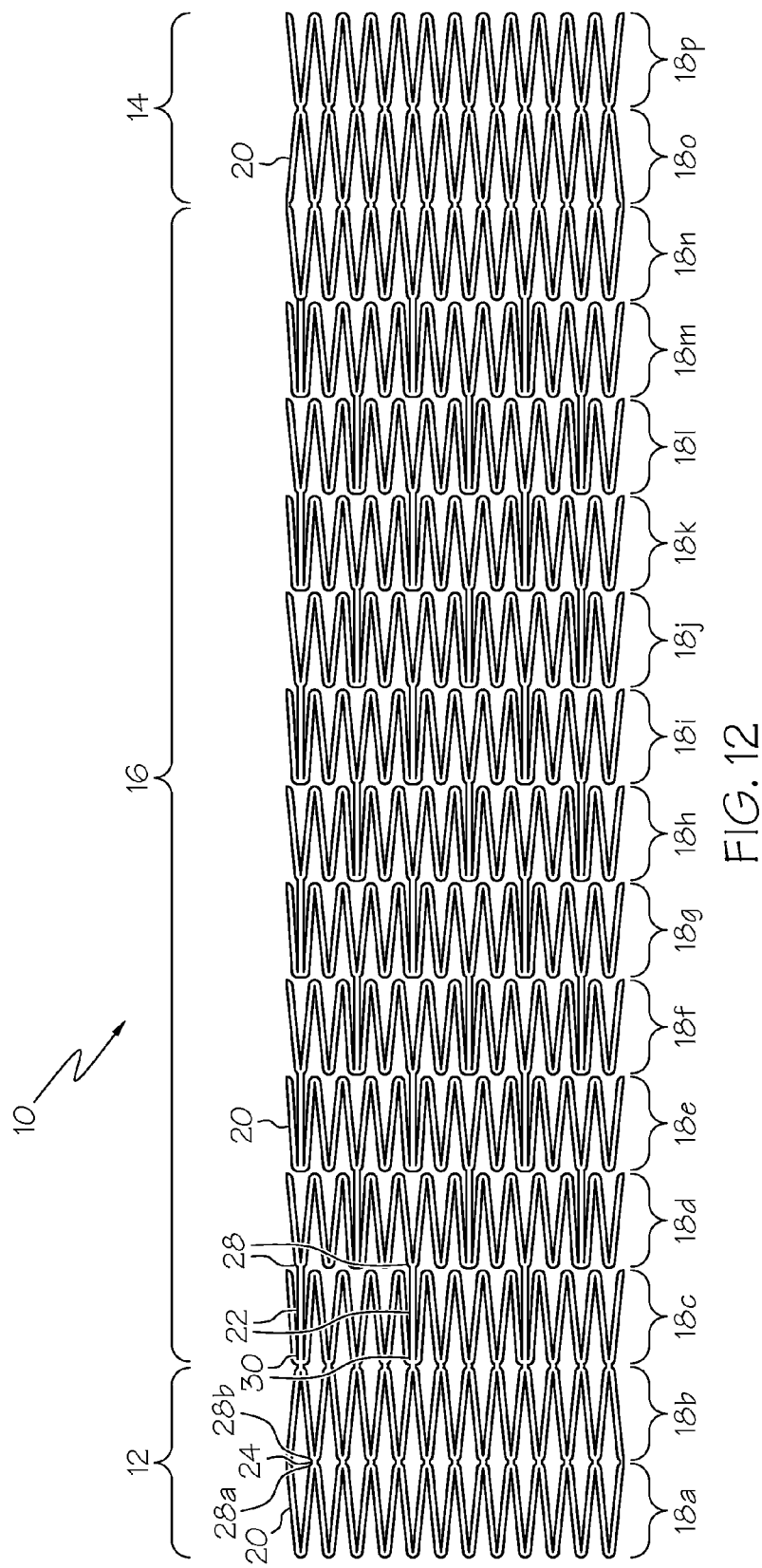
FIG. 12 is a rolled out view of an embodiment of the invention.
Figure 13:
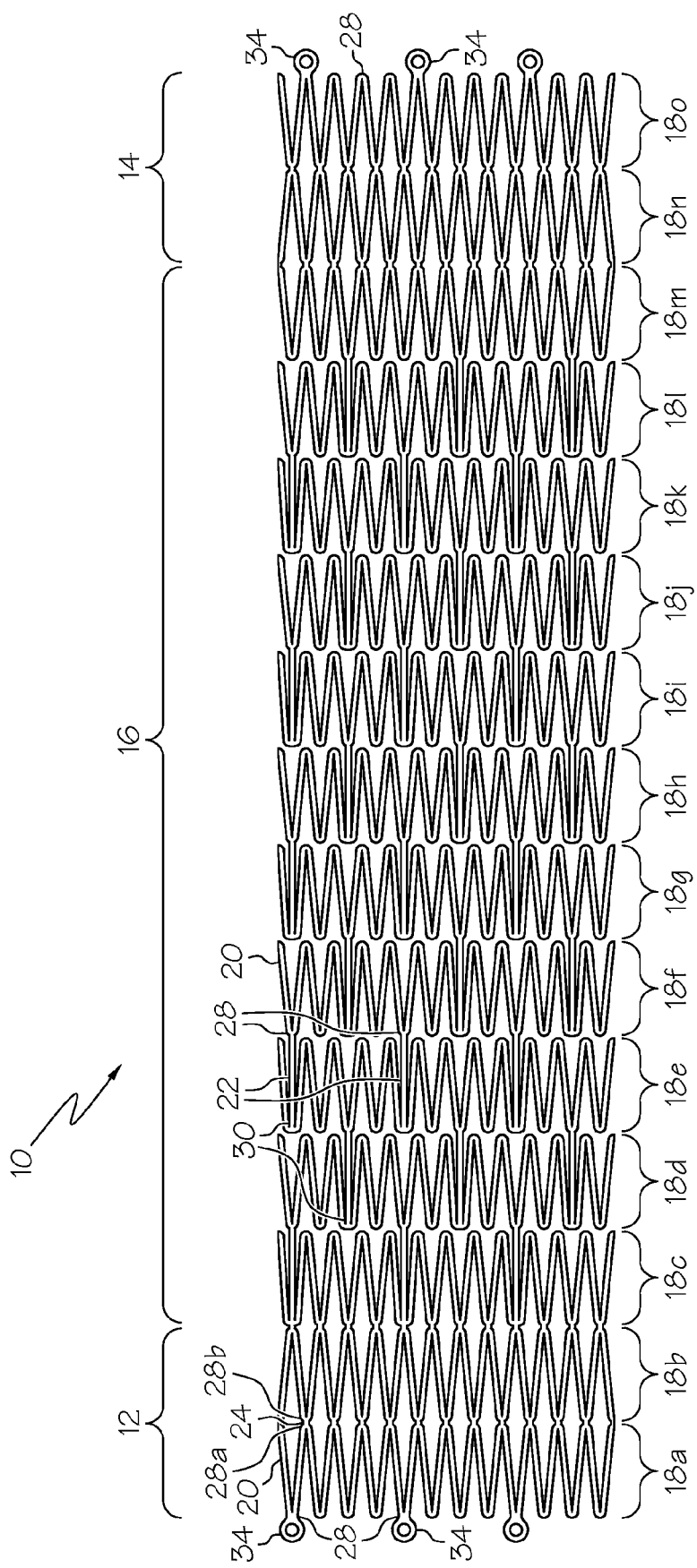
FIG. 13 is a rolled out view of an embodiment of the invention.

The stents 10 in FIGS. 12 and 13 have a proximal section 12, a middle section 16 and a distal section 14 formed by a plurality of circumferential rings 18. In FIG. 12, the stent 10 has sixteen (16) circumferential rings 18a-p while the stent 10 in FIG. 13 has fifteen (15) circumferential rings 18a-o. Thus, depending on the length of the stent 10 required for a particular anatomy, the total number of circumferential rings 18 can be varied.

Unlike the previous embodiments, where the stents 10 had alternating peak to peak connectors 24 and peak to valley connectors 22, the stents 10 of FIGS. 12 and 13 alternate the type of connector 22,24 used between the sections 12,14,16. Thus, the stent 10 has peak to peak 24 connectors engaging the circumferential rings 18*a-b* and 18*o-p* of both the proximal section 12 and the distal section 14 and peak to valley connectors 22 engaging the circumferential rings 18*c-n* of the middle section 16. It is within the scope of the invention for the stent 10 to have peak to valley 22 connectors engaging the circumferential rings 18*a-b* and 18*o-p* of both the proximal section 12 and the distal section 14 and peak to peak connectors 24 engaging the circumferential rings 18*c-n* of the middle section 16.

In FIGS. 12 and 13, both the proximal end sections 12 and the distal end sections 14 have two circumferential rings 18*a,b* and 18*o,p*. However, it is within the scope of the invention for the proximal and distal end sections 12,14 to have one, two, three, four, five, six, seven, eight, nine, ten or more circumferential rings 18.

Note that there is a one to one ratio of peak to peak connectors 24 to peaks 28 of the circumferential rings 18 forming the proximal section 12 and the distal section 14. As shown in FIG. 12, the first ends of the peak to peak connectors 24 engage each peak 28*a* of the first circumferential ring 18*a* to each peak 28*b* of the second circumferential ring 18*b* and similarly, the fifteenth circumferential ring 18*o* to the sixteenth circumferential ring 18*p*. Peak to peak connectors 24 also engage each peak 28 of the distal circumferential ring 18 of the proximal section 12 to each peak 28 of the proximal circumferential ring 18 of the middle section 16 and each peak 28 of the proximal circumferential ring 18 of the distal section 14 to each peak 28 of the distal circumferential ring 18 of the middle section 16. Thus, the number of peak to peak connectors 24 equals the number of peaks 18 of adjacent circumferential rings 18 of adjacent sections 12,14,16.

It is within the scope of the invention for the number of peak to peak connectors 24 to be less than the number of peaks 28 in adjacent circumferential rings 18, leaving some of the peaks 28 with no connector 24 attached. As shown in FIG. 12, there are an equal number of struts 20 in each circumferential ring 18 of the proximal section 12, middle section 16, and distal section 14 of the stent 10. However, it is within the scope of the invention for the number of struts 20 of the circumferential rings 18 of the proximal section 12 and/or the distal section 14 to be different than the number of struts 20 in the circumferential rings 18 of the middle section 16. In this case, there will be fewer peak to peak connectors 24 than there are peaks 28 between the proximal section 12 and the middle section 16 and/or the distal section 14 and the middle section 16. Although the embodiments described in FIGS. 1-11 do not have a proximal or a distal section 12,14 (as in the manner of the embodiment of FIG. 12), it is within the scope of the invention for a proximal and/or distal section 12,14 to be added to any of the inventive stent embodiments.

The middle sections 16 of the stents 10 in FIGS. 12 and 13 have a plurality of circumferential rings 18. In FIG. 12, the middle section 16 has twelve circumferential rings 18*c-n*, while the middle section 16 in FIG. 13 has eleven circumferential rings 18*c-l*. Adjacent circumferential rings 18 of the middle section 16 are engaged by peak to valley connectors 22. Eight struts 20, or four strut pairs, separate the first ends of the peak to valley connectors 22 engaged to the valleys 30 of the circumferential rings 18*c-n* and eight struts 20, or four strut pairs, separate the second ends of the peak to valley connectors 22 engaged to the peaks 28 of the circumferential rings 18*c-n*. The ratio of the strut pairs to connectors is four (strut pairs) to one (connector). Four struts 20, or two strut pairs, separate the second ends of the peak to valley connectors 22 from the first ends of adjacent peak to valley connectors 22 in a given circumferential ring (e.g. 18*e*, 18*f*, etc.). One example of adjacent peak to valley connectors 22 are the peak to valley connectors 22 engaging the third circumferential ring 18*c* to the fourth circumferential ring 18*d* and the peak to valley connectors 22 engaging the fourth circumferential ring 18*d* to the fifth circumferential ring 18*e*.

In at least one embodiment, the stent 10 may include one or more areas, bands, markers, coatings, members, etc. that is (are) detectable by imaging modalities such as X-Ray, MRI, ultrasound, etc. In some embodiments at least a portion of the stent 10 is at least partially radiopaque. It is within the scope of the invention for the stent 10 to have one, two, three, four, five, six, seven, eight, nine, ten, eleven, twelve, thirteen, fourteen, fifteen, sixteen, seventeen, eighteen, nineteen, twenty, or more radiopaque portions 34. In at least one embodiment, the radiopaque portions 34 are positioned at the proximal end, the distal end, or both the proximal and distal ends of the stent 10, as shown in FIG. 13.

In at least one embodiment, the radiopaque portions 34 are in the form of radiopaque paddles 34, as shown in FIG. 13. The stent 10 in FIG. 13 has radiopaque paddles 34 engaged to the peaks 28 of the struts 20 forming the outermost circumferential ring 18 of both the proximal end and the distal end of the stent 10. In this embodiment, the proximal end and the distal ends have the same number of radiopaque paddles 34 but it is within the scope of the invention for the proximal and distal ends to have different numbers of radiopaque paddles 34. In this embodiment, there are three peaks 28 between each radiopaque paddle 34 and three radiopaque paddles 34 on the proximal and distal ends of the stent 10, for a total of six radiopaque paddles 34. It is within the scope of the invention for the proximal end of the stent 10 to have a different number of peaks 28 between the radiopaque paddles 34 than the distal end of the stent 10.

Those skilled in the art will recognize that the stent 10 embodiments, illustrated and described herein are just some examples. Many stent designs can be developed where the connectors 22,24 are evenly spaced about the circumference of the stent 10. Furthermore, the first circumferential ring of connectors need not be peak to valley connectors but can be peak to peak connectors.

The following numbered statements characterize the embodiments described above:

1. A stent, the stent comprising at least three circumferential rings of struts, at least two circumferential rings of connectors, each circumferential ring of struts comprising a plurality of struts, each circumferential ring of connectors comprising at least two connectors, the at least three circumferential rings of struts alternating with the at least two circumferential rings of connectors, the at least two circumferential rings of connectors engaging adjacent circumferential rings of struts, the at least two circumferential rings of connectors alternating between circumferential rings of peak to valley connectors and circumferential rings of peak to peak connectors, each of the at least two connectors in a circumferential ring of connectors having a first end engaged to an adjacent circumferential ring of struts so that an equal number of struts separate each first end of each of the at least two connectors.

2. The stent of statement 1, the peak to valley connectors each having a bend.

3. The stent of statement 1, the peak to peak connectors each extending radially from the second circumferential ring to the third circumferential ring.

4. The stent of statement 1, the peak to peak connectors each having a bend.

5. The stent of statement 1, the struts of each circumferential ring each having a length, the length of struts of adjacent circumferential rings being different.

6. The stent of statement 1, further wherein at least a portion of the stent is radiopaque.

In some embodiments the stent 10 or one more portions thereof is configured to have a tapered inner and/or outer diameter along its length. The tapered configuration is provided by any number of known mechanisms such as by heat setting the stent or portion(s) thereof; the length of struts, and/or connectors in a given region(s) of the stent can be shortened or lengthened relative to those longitudinally adjacent thereto; providing a varied thickness to the struts and or connectors, etc.

In some embodiments one or both end regions of the stent is provided with a flared diameter relative to the middle region of the stent.

The inventive stents may be made from any suitable biocompatible materials including one or more polymers, one or more metals or combinations of polymer(s) and metal(s). Examples of suitable materials include biodegradable or bioabsorbable materials that are also biocompatible. By biodegradable is meant that a material will undergo breakdown or decomposition into harmless compounds as part of a normal biological process. Suitable biodegradable materials include polylactic acid, polyglycolic acid (PGA), collagen or other connective proteins or natural materials, polycaprolactone, hylauric acid, adhesive proteins, co-polymers of these materials as well as composites and combinations thereof and combinations of other biodegradable polymers. Other polymers that may be used include polyester and polycarbonate copolymers. Examples of suitable metals include, but are not limited to, stainless steel, titanium, tantalum, platinum, tungsten, gold and alloys of any of the above-mentioned metals. Examples of suitable alloys include platinum-iridium alloys, cobalt-chromium alloys including Elgiloy and Phynox, MP35N alloy and nickel-titanium alloys, for example, Nitinol.

The inventive stents may be made of shape memory materials such as superelastic Nitinol or spring steel, or may be made of materials which are plastically deformable. In the case of shape memory materials, the stent may be provided with a memorized shape and then deformed to a reduced diameter shape. The stent may restore itself to its memorized shape upon being heated to a transition temperature and having any restraints removed therefrom.

The inventive stents may be created by methods including cutting or etching a design from a tubular stock, from a flat sheet which is cut or etched and which is subsequently rolled or from one or more interwoven wires or braids. Any other suitable technique which is known in the art or which is subsequently developed may also be used to manufacture the inventive stents disclosed herein.

In some embodiments at least a portion of the stent is configured to include one or more mechanisms for the delivery of a therapeutic agent. Often the agent will be in the form of a coating or other layer (or layers) of material placed on a surface region of the stent, which is adapted to be released at the site of the stent's implantation or areas adjacent thereto.

A therapeutic agent may be a drug or other pharmaceutical product such as non-genetic agents, genetic agents, cellular material, etc. Some examples of suitable non-genetic therapeutic agents include but are not limited to: anti-thrombogenic agents such as heparin, heparin derivatives, vascular cell growth promoters, growth factor inhibitors, Paclitaxel, etc. Some other examples of therapeutic agents include everolimus and sirolimus, their analogs and conjugates. Where an agent includes a genetic therapeutic agent, such a genetic agent may include but is not limited to: DNA, RNA and their respective derivatives and/or components; hedgehog proteins, etc. Where a therapeutic agent includes cellular material, the cellular material may include but is not limited to: cells of human origin and/or non-human origin as well as their respective components and/or derivatives thereof. Where the therapeutic agent includes a polymer agent, the polymer agent may be a polystyrene-polyisobutylene-polystyrene triblock copolymer (SIBS), polyethylene oxide, silicone rubber and/or any other suitable substrate.

The above disclosure is intended to be illustrative and not exhaustive. This description will suggest many variations and alternatives to one of ordinary skill in this art. The various elements shown in the individual figures and described above may be combined or modified for combination as desired. All these alternatives and variations are intended to be included within the scope of the claims where the term "comprising" means "including, but not limited to".

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

This completes the description of the invention. Those skilled in the art may recognize other equivalents to the specific embodiment described herein which equivalents are intended to be encompassed by the claims attached hereto.

The invention claimed is:

1. A stent, the stent comprising:
    a first circumferential ring, a second circumferential ring, and a third circumferential ring, adjacent circumferential rings forming a first ring pair and a second ring pair, each circumferential ring comprising a plurality of struts;
    a first peak to valley connector, and a second peak to valley connector, the peak to valley connectors each engaging the first ring pair, the peak to valley connectors each having a first end, each of the first ends of the peak to valley connectors separated by a first number of struts in a first circumferential direction; and
    a first peak to peak connector, and a second peak to peak connector, the peak to peak connectors each engaging the second ring pair, the peak to peak connectors each having a first end, each of the first ends of the peak to peak connectors separated by a second number of struts in the first circumferential direction.

2. The stent of claim 1, the first number of struts different from the second number of struts.

3. The stent of claim 1, further comprising a third peak to valley connector and a third peak to peak connector.

4. The stent of claim 3, the first number of struts equal to ten and the second number of struts equal to eight.

5. The stent of claim 1, the peak to valley connectors each having a bend.

6. The stent of claim 1, the peak to peak connectors each extending circumferentially from the second circumferential ring to the third circumferential ring.

7. The stent of claim 1, the peak to peak connectors each having a bend.

8. The stent of claim 1, the struts of the first circumferential ring each having a first length, the struts of the second circumferential ring each having a second length, the first length different than the second length.

9. The stent of claim 1, wherein the peak to peak connectors extend substantially parallel to the longitudinal axis of the stent.

10. A stent, the stent comprising a first circumferential ring, a second circumferential ring, a third circumferential ring, at least two peak to valley connectors and at least two peak to peak connectors, each circumferential ring comprising a plurality of struts,
the at least two peak to valley connectors engaging the first circumferential ring to the second circumferential ring, each of the at least two peak to valley connectors having a first end, an equal number of struts separating the first ends of the at least two peak to valley connectors in a first circumferential direction, and
the at least two peak to peak connectors engaging the second circumferential ring to the third circumferential ring, each of the at least two peak to peak connectors having a first end, an equal number of struts separating the first ends of the at least two peak to peak connectors in the first circumferential direction.

11. The stent of claim 10, the peak to valley connectors each having a bend.

12. The stent of claim 10, the peak to peak connectors each extending circumferentially from the second circumferential ring to the third circumferential ring.

13. The stent of claim 10, the peak to peak connectors each having a bend.

14. The stent of claim 10, the struts of the first circumferential ring each having a first length, the struts of the second circumferential ring each having a second length, the first length different than the second length.

15. The stent of claim 10, wherein the peak to peak connectors extend substantially parallel to the longitudinal axis of the stent.

16. A stent, the stent comprising:
a proximal section, the proximal section comprising a first circumferential ring, a second circumferential ring and a plurality of peak to peak connectors, each circumferential ring comprising a plurality of struts, each of the plurality of peak to peak connectors having a first end and a second end, each of the first ends of the plurality of peak to peak connectors separated by two of the plurality of struts, and each of the second ends of the plurality of peak to peak connectors separated by two of the plurality of struts;
a middle section, the middle section comprising a plurality of circumferential rings and a plurality of peak to valley connectors, adjacent circumferential rings being engaged by the plurality of peak to valley connectors;
a distal section, the distal section comprising a first circumferential ring, a second circumferential ring, and a plurality of peak to peak connectors, each circumferential ring comprising a plurality of struts, each of the plurality of peak to peak connectors having a first end and a second end, each of the first ends of the plurality of peak to peak connectors separated by two of the plurality of struts, and each of the second ends of the plurality of peak to peak connectors separated by two of the plurality of struts;
a first plurality of peak to peak connectors, the first plurality of peak to peak connectors engaging the proximal section and the middle section; and
a second plurality of peak to peak connectors, the second plurality of peak to peak connectors engaging the middle section and the distal section.

17. The stent of claim 16, the first plurality of peak to peak connectors engaging the second circumferential ring of the proximal section to a proximal circumferential ring of the middle section, the second circumferential ring of the proximal section comprising a plurality of distal peaks, the proximal circumferential ring of the middle section comprising a plurality of proximal peaks, the first plurality of peak to peak connectors, the plurality of distal peaks and the plurality of proximal peaks being equal.

18. The stent of claim 17, the second plurality of peak to peak connectors engaging the first circumferential ring of the distal section to a distal circumferential ring of the middle section, the first circumferential ring of the distal section comprising a plurality of proximal peaks, the distal circumferential ring of the middle section comprising a plurality of distal peaks, the second plurality of peak to peak connectors, the plurality of proximal peaks and the plurality of distal peaks being equal.

19. The stent of claim 16, each of the plurality of circumferential rings of the middle section comprising a plurality of struts, the plurality of peak to valley connectors of the middle section each having a first end and a second end, each of the first ends of the plurality of peak to valley connectors being separated by eight struts, and the second end of a peak to valley connector being separated by four struts from the first end of an adjacent peak to valley connector in a circumferential ring of the middle section.

20. The stent of claim 16, wherein the peak to peak connectors extend substantially parallel to the longitudinal axis of the stent.

* * * * *